(12) United States Patent
Savran et al.

(10) Patent No.: US 9,341,621 B2
(45) Date of Patent: May 17, 2016

(54) ULTRASENSITIVE DETECTION OF BIOMOLECULES USING IMMUNOSEPARATION AND DIFFRACTOMETRY

(75) Inventors: Cagri Savran, West Lafayette, IN (US); Philip Low, West Lafayette, IN (US); David Thompson, West Lafayette, IN (US); Walter Henne, West Lafayette, IN (US); Derek Doorneweerd, West Lafayette, IN (US); Chun-Li Chang, West Lafayette, IN (US); Ghanashyam Acharya, West Lafayette, IN (US); David Brownholland, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 709 days.

(21) Appl. No.: 12/601,986

(22) PCT Filed: May 29, 2008

(86) PCT No.: PCT/US2008/065092
§ 371 (c)(1),
(2), (4) Date: Sep. 7, 2010

(87) PCT Pub. No.: WO2008/150873
PCT Pub. Date: Dec. 11, 2008

(65) Prior Publication Data
US 2010/0330702 A1 Dec. 30, 2010

Related U.S. Application Data

(60) Provisional application No. 60/932,471, filed on May 31, 2007, provisional application No. 60/986,051, filed on Nov. 7, 2007.

(51) Int. Cl.
*G01N 33/53* (2006.01)
*G01N 33/543* (2006.01)
(Continued)

(52) U.S. Cl.
CPC ........ *G01N 33/54386* (2013.01); *C12Q 1/6804* (2013.01); *G01N 21/4788* (2013.01); *G01N 33/54393* (2013.01)

(58) Field of Classification Search
CPC ............... G01N 33/54373; G01N 21/4788; G01N 21/7743; G01N 21/774; G02B 5/1809
USPC ............ 435/7.94, 288.7, 808; 436/501, 436/523–527, 536, 538–540; 422/82.11, 422/82.05; 356/305; 385/12
See application file for complete search history.

(56) References Cited

U.S. PATENT DOCUMENTS

| | | |
|---|---|---|
| 5,029,981 A | 7/1991 | Thompson |
| 5,335,113 A | 8/1994 | Jackson et al. |

(Continued)

FOREIGN PATENT DOCUMENTS

WO    WO 2008/150873 A1    12/2008

OTHER PUBLICATIONS

Gerbhardt et al., RNA Aptamers to S-Adenosylhomocysteine: Kinetic Properties, Divalent Cation Dependency, and Comparison with Anti-S-adenosylhomocysteine Antibody, 2000, Biochemistry, vol. 39, No. 24, pp. 7255-7265.*

(Continued)

*Primary Examiner* — Erik B Crawford
(74) *Attorney, Agent, or Firm* — Maginot, Moore & Beck, LLP

(57) ABSTRACT

Systems and methods for rapid and ultrasensitive detection of target biomolecules in a sample are presented. The detection of biomolecules is achieved through a synergistic use of immunoseparation and diffractometry, and the formation of antibody-biomolecule-ligand sandwich complexes that form diffraction gratings. Characteristic diffraction patterns are then produced upon illumination of the diffraction gratings with light. The diffraction patterns can be used to detect very low amounts of biomolecules present in the sample.

17 Claims, 12 Drawing Sheets

(51) Int. Cl.
*C12Q 1/68* (2006.01)
*G01N 21/47* (2006.01)

(56) References Cited

U.S. PATENT DOCUMENTS

| | | | |
|---|---|---|---|
| 5,363,238 | A | 11/1994 | Akune et al. |
| 5,629,804 | A | 5/1997 | Tomono |
| 6,436,651 | B1 | 8/2002 | Everhart et al. |
| 2001/0004526 | A1 | 6/2001 | Everhart et al. |
| 2003/0017581 | A1* | 1/2003 | Li et al. ............... 435/287.2 |
| 2005/0287681 | A1* | 12/2005 | Nishiuma et al. ............ 436/524 |
| 2006/0014172 | A1 | 1/2006 | Muller et al. |
| 2007/0070355 | A1* | 3/2007 | Cunningham et al. ........ 356/454 |
| 2007/0298513 | A1* | 12/2007 | Starzl et al. .................. 436/164 |

OTHER PUBLICATIONS

International Search Report and Written Opinion for International Patent Application No. PCT/US2008/065092 dated Oct. 31, 2008.
Acharya, G.; Chang, C.-L.; Doorneweerd, D.D.; Vlashi, E.; Henne, W.A.; Hartmann, L.C.; Low, P.S.; Savran, C.A. "Immunomagnetic Diffractometry for Detection of Diagnostic Serum Markers," *J. Am. Chem. Soc.*, 2007, 129, 15824-15829.
Bailey, R.C.; Nam, J.-M.; Mirkin, C.A.; Hupp, J.T. "Real-Time Multicolor DNA Detection With Chemoresponsive Diffraction Gratings and Nanoparticle Probes," *J. Am. Chem. Soc.*, 2003, 125, 13541-13547.
Bao, Y.P.; Wei, T.-F.; Lefebvre, P.A.; An, H.; He, L.; Kunkel, G.T.; Muller, U.R. "Detection of Protein Analytes Via Nanoparticle-Based Bio Bar Code Technology," *Anal. Chem.*, 2006, 78, 2055-2059.
Brandenburg, A.; Krauter, R.; Künzel, C.; Stefan, M.; Schulte, H. "Interferometric Sensor for Detection of Surface-Bound Bioreactions," *Appl. Optics*, 2000, 39, 6396-6405.
Capitán-Vallvey, L.F.; Duque, O.; Mirón-García, G.; Checa-Moreno, R. "Determination of Protein Content Using a Solid Phase Spectrophotometric Procedure," *Anal. Chim. Acta*, 2001, 433, 155-163.
Chang, C.-L.; Acharya, G.; Savran, C.A. "In situ Assembled Diffraction Grating for Biomolecular Detection," *Appl. Phys. Lett.*, 2007, 90, 233901-1-233901-3.
Chen, H.; Wang, L.; Wang, L.; Wang, G.; Li, L.; Xu, F. "Preparation of Novel Composite Nanoclusters and Their Application in the Ultrasensitive Detection of Proteins," *Anal. Chim. Acta*, 2004, 521, 9-15.
de la Escosura-Muñiz, A.; González-García, M.B.; Costa-García, A. "Electrocatalytic Detection of Aurothiomalate on Carbon Electrodes Application as a Non-Enzymatic Label to the Quantification of Proteins," *Anal. Chim. Acta*, 2004, 524, 355-363.
Díaz-González, M.; Hernández-Santos, D.; González-García, M.B.; Costa-García, A. "Development of an Immunosensor for the Determination of Rabbit IgG Using Streptavidin Modified Screen-Printed Carbon Electrodes," *Talanta*, 2005, 65, 565-573.
Eichner, E.R.; McDonald, C.R.; Dickson, V.L. "Elevated Serum Levels of Unsaturated Folate Binding Protein: Clinical Correlates in a General Hospital Population," *Am. J. Clin. Nutr.*, 1978, 31, 1988-1992.
Frost; M.C.; Meyerhoff, M.E. "Implantable Chemical Sensors for Real-Time Clinical Monitoring: Progress and Challenges," *Curr. Opin. Chem. Biol.*, 2002, 6, 633-641.
Gellekink, H.; van Oppenraaij-Emmerzaal, D.; van Rooij, A.; Struys, E.A.; den Heijer, M.; Blom, H.J. "Stable-Isotope Dilution Liquid Chromatography-Electrospray Injection Tandem Mass Spectrometry Method for Fast, Selective Measurement of *S*-Adenosylmethionine and *S*-Adenosylhomocysteine in Plasma," *Clin. Chem.*, 2005, 51, 1487-1492.
Goh, J.B.; Tam, P.L.; Loo, R.W.; Goh, M.C. "A Quantitative Diffraction-Based Sandwich Immunoassay," *Anal. Biochem.*, 2003, 313, 262-266.

Guo, Z.-X.; Hao, Y.-M.; Cong, X.; Shen, H.-X. "Application of the Dibromohydroxyphenylfluorone-Molybdenum(VI) Complex to the Sensitive Spectrophotometric Determination of Protein," *Anal. Chim. Acta*, 2000, 403, 225-233.
Haukanes, B.-I.; Kvam, C. "Application of Magnetic Beads in Bioassays," *Bio/Technology*, 1993, 11, 60-63.
Henne, W.A.; Doorneweerd, D.D.; Lee, J.; Low, P.S.; Savran, C. "Detection of Folate Binding Protein With Enhanced Sensitivity Using a Functionalized Quartz Crystal Microbalance Sensor," *Anal. Chem.*, 2006, 78, 4880-4884.
Indyk, H.E.; Filonzi, E.L. "Direct Optical Biosensor Analysis of Folate-Binding Protein in Milk," *J. Agric. Food Chem.*, 2004, 52, 3253-3258.
Kricka, L.J. "Miniaturization of Analytical Systems," *Clin. Chem.*, 1998, 44, 2008-2014.
Loo, R.W.; Tam, P.L.; Goh, J.B.; Goh, M.C. "An-Enzyme-Amplified Diffraction-Based Immunoassay," *Anal. Biochem.*, 2005, 337, 338-342.
Palaček, E.; Masařík, M.; Kizek, R.; Kuhlmeier, D.; Hassmann, J.; Schülein, J. "Sensitive Electrochemical Determination of Unlabeled MutS Protein and Detection of Point Mutations in DNA," *Anal. Chem.*, 2004, 76, 5930-5936.
Renault, J.P.; Bernard, A.; Juncker, D.; Michel, B.; Bosshard, H.R.; Delamarche, E. "Fabricating Microarrays of Functional Proteins Using Affinity Contact Printing," *Angew. Chem. Int. Ed.*, 2002, 41, 2320-2323.
Riganti, L.; Matteoni, C.; Di Angelantonio, S.; Nistri, A.; Gaimarri, A.; Sparatore, F.; Canu-Boido, C.; Clementi, F.; Gotti, C. "Long-Term Exposure to the New Nicotinic Antagonist 1,2-bis*N*-cytisinylethane Upregulates Nicotinic Receptor Subtypes of SH-SY5Y Human Neuroblastoma Cells," *British J. Pharmacol.*, 2005, 146, 1096-1109.
Salyan, M.E.K.; Pedicord, D.L.; Bergeron, L.; Mintier, G.A.; Hunihan, L.; Kuit, K.; Balanda, L.A.; Robertson, B.J.; Feder, J.N.; Westphal, R.; Shipkova, P.A.; Blat, Y. "A General Liquid Chromatography/Mass Spectroscopy-Based Assay for Detection and Quantitation of Methyltransferase Activity," *Anal. Biochem.*, 2006, 349, 112-117.
Sbrana, E.; Bramanti, E.; Spinetti, M.C.; Raspi, G. "*S*-Adenosyl Methionine/*S*-Adenosyl-L-Homocysteine Ratio Determination by Capillary Electrophoresis Employed as a Monitoring Tool for the Antiviral Effectiveness of Adenosine Analogs," *Electrophoresis*, 2004, 25, 1518-1521.
Seydack, M. "Nanoparticle Labels in Immunosensing Using Optical Detection Methods," *Biosensors and Bioelectronics*, 2005, 20, 2454-2469.
Smith, P.K.; Krohn, R.I.; Hermanson, G.T.; Mallia, A.K.; Gartner, F.H.; Provenzano, M.D.; Fujimoto, E.K.; Goeke, N.M.; Olson, B.J.; Klenk, D.C. "Measurement of Protein Using Bicinchoninic Acid," *Anal. Biochem.*, 1985, 150, 76-85.
Tsukagoshi, K.; Nakahama, K.; Nakajima, R. "Direct Detection of Biomolecules in a Capillary Electrophoresis-Chemiluminescence Detection System," *Anal. Chem.*, 2004, 76, 4410-4415.
Urdea, M.; Penny, L.A.; Olmsted, S.S.; Giovanni, M.Y.; Kaspar, P.; Shepherd, A.; Wilson, P.; Dahl, C.A.; Buchsbaum, S.; Moeller, G.; Hay Burgess, D.C. "Requirements for High Impact Diagnostics in the Developing World," *Nature*, 2006, 444, 73-79.
Wang, C.; Leffler, S.; Thompson, D.H.; Hrycyna, C.A. "A General Fluorescence-Based Coupled Assay for *S*-Adenosylmethionine-Dependent Methyltransferases," *Biochem. Biophys. Res. Comm.*, 2005, 331, 351-356.
Xia, Y.; Whitesides, G.M. "Soft Lithography," *Annu. Rev. Mater. Sci.*, 1998, 28, 153-184.
Yi, P.; Melnyk, S.; Pogribna, M.; Pogribny, I.P.; Hine, R.J.; James, S.J. "Increase in Plasma Homocysteine Associated With Parallel Increases in Plasma *S*-Adenosylhomocysteine and Lymphocyte DNA Hypomethylation," *J. Biol. Chem.*, 2000, 275, 29318-29323.

* cited by examiner

ULTRASENSITIVE DETECTION OF BIOMOLECULES USING IMMUNOSEPARATION AND DIFFRACTOMETRY

CROSS-REFERENCE TO RELATED APPLICATIONS

This application is a §371 filing based on PCT/JP2008/065092, filed May 29, 2008, and claims priority to U.S. Provisional Patent Application Ser. No. 60/932,471, filed May 31, 2007, and 60/986,051, filed Nov. 7, 2007. The disclosure of each of these applications is incorporated by reference herein in its entirety.

GOVERNMENT INTERESTS

This invention was made with United States government support under grant No. NCC 2-1363 awarded by the National Aeronautics and Space Administration and grant No. NIHCA112427 awarded by the National Institutes of Health. The United States government has certain rights in this invention.

TECHNICAL FIELD

The present invention generally relates to the field of characterization of biomolecules, and particularly to the detection of biomolecules using immunomagnetic diffractometry.

BACKGROUND

A major application of nanomedicine lies in the early detection of biomolecules (biological molecules) that are molecular markers of malignant diseases. Methods currently available for detection of disease biomarkers include fluorescence immunoassays, enzyme-linked immunosorbent assays (ELISA), PCR approaches, biobarcode assays, quartz crystal microbalance analyses, electrochemical methods, microcantilever detection, and nanoparticle-based biosensors. Despite the diversity of available detection platforms, important challenges still remain in minimizing sensor size, reducing detection time, eliminating target labeling requirements, minimizing signal amplification steps, and developing simple and inexpensive fabrication protocols.

Quantitative characterization of biomolecules, such as metabolic intermediates, proteins, lipids, and nucleic acids, is a critical aspect of molecular diagnostics and drug development (Urdea et al., 2006, *Nature* 444: 73-79; Frost et al., 2002, *Curr. Opin. Chem. Biol.* 6: 633-641). A number of assays based on spectrophotometry, fluorometry, chemiluminiscence, and electrochemical immunoassays have been reported for biomolecular detection (Capitan-Vallvey, 2001, *Anal. Chim. Acta* 433: 155-163; Guo et al., 2000, *Anal. Chim. Acta* 403: 225-233; Chen et al., 2004, *Anal. Chim. Acta* 521: 9-15; Tsukagoshi et al., 2004, *Anal. Chem.* 76: 4410-4415; de la Escosura-Muniz et al., 2004, *Anal. Chim. Acta* 524: 355-363; Palecek et al., 2004, *Anal. Chem.* 76: 5930-5936; Diaz-Gonzalez et al., 2005, *Talanta* 65: 565-573). These methods are effective, but are often slow due to multiple sample pretreatment steps that may increase labor, time, and cost of the analysis. Immunoassays that combine high sensitivity with fast, robust, and inexpensive methodologies for biomolecular detection and analysis are of growing importance (Kricka, 1998, *Clin. Chem.* 44: 2008-2014). One such example is the biosensor for the detection of S-adenosyl homocysteine (SAH), a diagnostic marker for cardiovascular disease (Melnyk et al., 2000, *J. Biol. Chem.* 275: 29318-29323).

Increased attention has recently been paid to the development and application of separation techniques that employ small magnetic beads to separate a desired analyte from a complex biological sample. Magnetic beads have been employed for DNA isolation (followed by PCR amplification), genomic analyses drug discovery, and affinity capture and purification of proteins and peptides. Also, magnetic beads coupled to Ni-NTA (nitrilotriacetic acid) ligands have been used in the magnetocapture, purification, and detection of histidine-tagged proteins. Although magnetic bead-based strategies have greatly improved analyte capture, their potential for biosensing applications is limited by the labor and time required to quantitate the captured biomarker. To this end, combining a one-step magnetic bead-based capture scheme with a fluorescence or radiolabel-free detection scheme would constitute a significant advance.

Biomolecular detection using optical diffraction gratings is a versatile label-free method (Brandenburg et al., 2000, *Appl. Optics* 39: 6396-6405). However, the microfabrication of diffraction gratings is a tedious and expensive step that limits its practical applicability (Bailey et al. 2003, *J. Am. Chem. Soc.* 125: 13541-13547). Also, most of the available diffraction grating-based detection methods require additional signal amplification steps (after the desired analyte is captured on a solid surface), such as the sequential use of nanoparticle-conjugated oligonucleotides or antibodies and/or the use of enzymes to improve the sensitivity of detection, leading to time-consuming, multi-step procedures (Loo et al., 2005, *Anal. Biochem.* 337: 338-342).

BRIEF SUMMARY

Systems for detecting biomolecules in samples are provided, which include: a plurality of biomolecule-specific first molecules; a plurality of biomolecule-specific second molecules microprinted on a substrate surface; an incident light source for delivering a beam to the substrate surface; and an optical detector for detecting the intensity of light reflected from the surface. The biomolecule-specific first molecules may bind the biomolecules in the sample to produce immune complexes. The substrate surface may be suitable for self-assembly of the second molecule-bound immune complexes in selected patterns. The first molecules may be antibodies or ligands. The second molecules may be antibodies or ligands. The substrate surfaces may be gold-coated glass slides. The light source may be laser. The biomolecule-specific first molecules may be attached to solid support. The biomolecule-specific first molecules may be attached to magnetic beads. The first molecules may include, e.g., antibodies against folate receptors or antibodies against S-adenosyl homocysteine (SAH). The biomolecules may, e.g., include S-adenosyl homocysteine (SAH) or folate receptors. The second molecules may include various ligands, e.g., adenosine-specific aptamers containing SEQ ID NO:1, or they may include folate coupled to bovine serum albumin (F-BSA).

Systems for detecting biomolecules in samples are provided, which include: substrates having a surface comprising a plurality of patternly disposed ligands; a plurality of sandwich complexes each having the ligand and a biomolecule-specific antibody provided so as to sandwich the biomolecule between the antibody and the ligand; an incident light source for delivering a beam to the substrate surface; and an optical detector for detecting the intensity of light reflected from the surface. The substrate surface may be suitable for self-assembly of the ligand-bound immune complexes in selected patterns. The substrate surfaces may be gold-coated glass slides. The light source may be laser. The biomolecule-specific antibodies may be attached to solid support. The biomolecule-specific antibodies may be attached to magnetic beads. The biomolecules may, e.g., include S-adenosyl homocysteine (SAH) or folate receptors. The ligands may include, e.g., adenosine-specific aptamers containing SEQ ID NO:1, or they may include folate coupled to bovine serum albumin (F-BSA).

Methods for detecting biomolecules in a sample are provided, which include: introducing biomolecule-specific first molecules to the sample containing the biomolecules to produce first molecule-biomolecule complexes through a binding interaction; providing a plurality of patternly disposed biomolecule-specific second molecules attached to a substrate surface; contacting the first molecule-biomolecule complexes with the plurality of biomolecule-specific second molecules to produce sandwich complexes that assemble in a pattern on the solid support surface; exposing the patterns of sandwich complexes to a light source; and measuring the intensity of light reflected from the substrate surface. In the practice of the methods, providing a plurality of patterned biomolecule-specific second molecules may include depositing micropatterns of second molecules on gold-coated glass slides using a microcontact printing process. Alternatively, providing a plurality of patterned biomolecule-specific second molecules may include applying a plurality of second molecules onto a polydimethylsiloxane (PDMS) stamp surface. In the practice of the methods, the first molecules may be antibodies or ligands. In the practice of the methods, the second molecules may be antibodies or ligands. The methods may include detection of S-adenosyl homocysteine (SAH) or folate receptors (FR).

DETAILED DESCRIPTION OF THE PRESENTLY PREFERRED EMBODIMENTS

The present invention is directed toward methods for ultra-sensitive detection of biomolecules by immunomagnetic diffractometry. A "biomolecule" is a molecule that naturally occurs in living organisms. Biomolecules primarily include carbon and hydrogen, along with nitrogen, oxygen, phosphorus and sulfur. Other elements may sometimes be incorporated but are less common. "Biomolecules" for the purposes of the present invention include, but are not limited to, single and double-stranded oligonucleotides, DNA, RNA, proteins, protein fragments, amino acids, peptides, aptamers, antibodies, antigens, lectins, carbohydrates, transcription factors, cellular components, cellular surface molecules, receptors, viruses, virus fragments, lipids, hormones, vitamins, and small molecules such as drugs.

The detection of biomolecules according to the present invention includes immunoseparation. As used herein, "immunoseparation" refers to the separation of target biomolecules from populations of various molecules using immunological separation techniques, including but not limited to immunoprecipitation, immunoimmobilization, immunoaffinity chromatography, immunomagnetism, and the like. Immunoseparation typically includes the use of biomolecule-specific antibodies and/or antibody fragments to form immune complexes. An "immune complex" is the combination of an epitope with an antibody directed against that epitope. For example, an immune complex, as used herein, refers to a complex that is formed by a target biomolecule (to be detected) and an antibody that is specific for that biomolecule. An overview of immunosensing and immunoseparation techniques is disclosed in Sadik and Dennison, 2001, *Immunosensing and Immunoseparation Technologies*, Wiley-Interscience. Example of immunoimmobilization of receptors by subunit-specific antibodies is disclosed in Riganti et al., 2005, *British J. Pharmacol.* 146: 1096-1109. Immunomagnetism is a technique that uses magnetism and immunoaffinity for the analysis and sorting of molecules and/or cells according to specific markers. Immunomagnetism includes the use of magnetic materials for affinity binding of desired molecules, and thus finds use in the purification of proteins and peptides.

Figure 1:
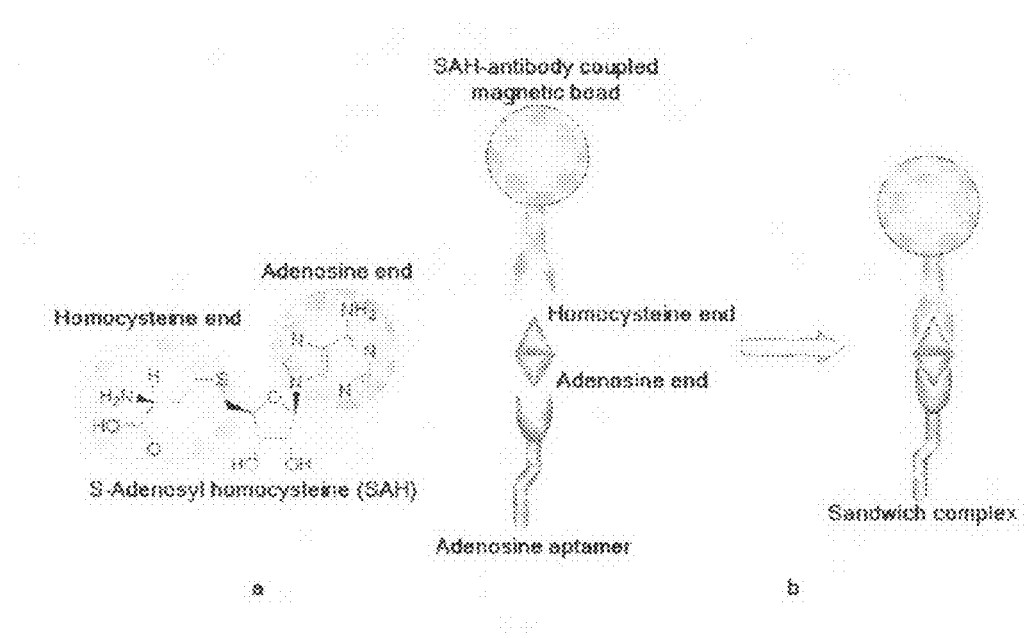
FIG. 1 is a schematic representation of one embodiment of the sandwich complex formation.
Figure 7:
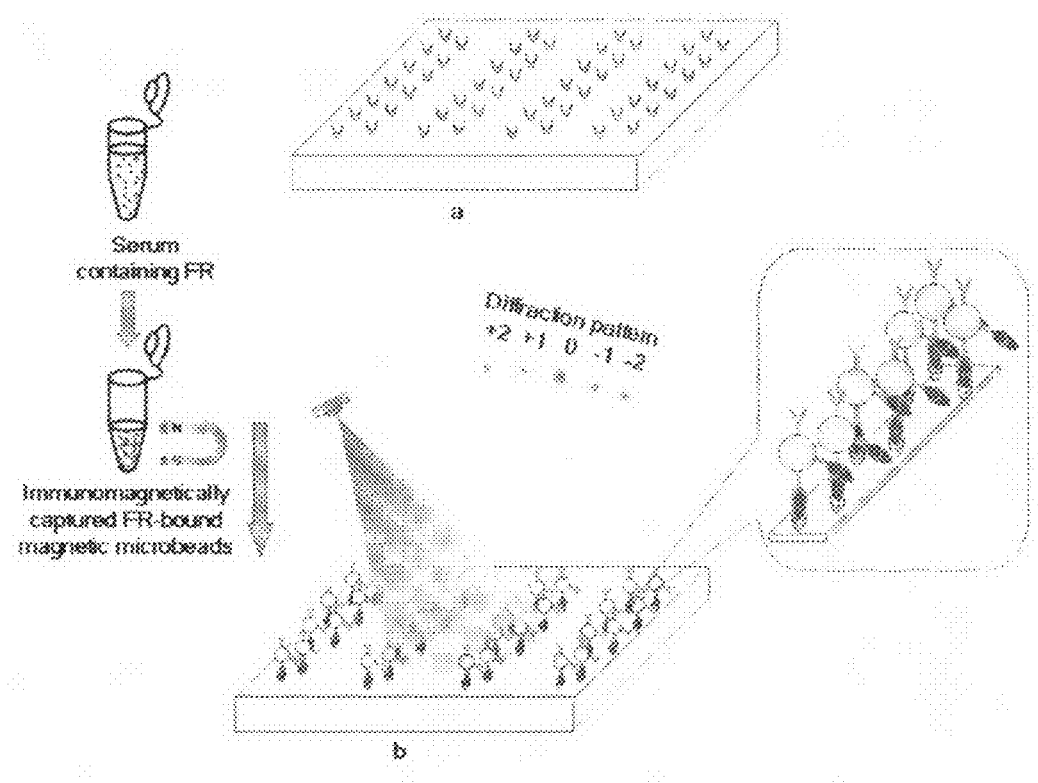
FIG. 7 is a schematic representation of immunomagnetic diffractometry and its application to detection of folate receptor (FR).

The present invention contemplates the creation of sandwich complexes. A "sandwich complex" refers to a form of a complex that is formed by the binding of the target biomolecule with at least two other molecules (herein referred to as a "first molecule" and a "second molecule"). The molecules that bind the target biomolecule to produce a sandwich complex may be identical, e.g. they may be two or more target biomolecule-specific antibodies (identical or not), or they may be two or more target biomolecule-specific ligands (identical or not). Alternatively, the molecules that bind the target biomolecule to produce a sandwich complex may be different, e.g. the first molecule may be an antibody, whereas the second molecule may be a ligand. Although the method is not limited to the specific molecules involved, of particular interest is a situation in which the first molecule that binds the target biomolecule is an antibody, and the second molecule that binds the target biomolecule is a ligand. In the example shown in FIG. 1, a sandwich complex can be formed by binding of the target biomolecule with both: 1) an antibody; and 2) a ligand. In this embodiment, the biomolecule act as an antigen which forms immune complex with a biomolecule-specific antibody, and this immune complex is attached, via the biomolecule, to a biomolecule-specific ligand. The biomolecule to be detected is thus "sandwiched" between the first molecule (e.g., biomolecule-specific antibody) and the second molecule (e.g., biomolecule-specific ligand), resulting in the formation of a sandwich complex with the configuration: antibody-biomolecule-ligand (FIG. 1b). The first molecules used in the practice of the present invention can be attached to solid support. For example, they can be antibodies that are attached to magnetic microbeads, as shown in FIG. 7. The second molecules (e.g., ligands) can also be anchored to solid support, and in particular they can be printed in the form of desired patterns (i.e. patternly disposed) onto surfaces that are suitable for diffractometry (FIG. 7), e.g. onto gold-coated glass slides. The term "solid support" or "solid phase support" refers to an inert material or molecule to which an antibody or a ligand may be bound or coupled, either directly or through a linking arm.

This invention contemplates the use of more than one type of antibody in the formation of antibody-biomolecule-ligand sandwich complexes. As well, the invention contemplates the use of more than one type of ligand in the formation of antibody-biomolecule-ligand sandwich complexes. The present invention contemplates the self-assembly of such sandwich complexes onto solid support surfaces. Such in situ assembled sandwiches can create patterns that function as diffraction gratings and can be used for diffraction intensity measurements. The diffraction intensity measurements are quantitatively correlated to the amount, i.e. concentration, of biomolecule in the sample that is being tested.

The present invention contemplates the use of antibodies immunologically specific for all or part, e.g., an amino-terminal portion, of the target biomolecule(s). "Antibodies," as used herein, includes polyclonal and monoclonal antibodies, chimeric, and single chain antibodies, as well as Fab fragments, including the products of a Fab or other immunoglobulin expression library. With respect to antibodies, the term "immunologically specific" refers to antibodies that bind to one or more epitopes of a protein of interest, but which do not substantially recognize and bind other molecules in a sample containing a mixed population of antigenic biological molecules. In some embodiments, the antibodies may be monoclonal. Alternatively, the antibodies may be polyclonal.

The term "ligand" refers to a molecule or group of molecules that bind to one or more specific sites of a biomolecule. The ligands useful for practicing the present invention are specific to the target (to be detected) biomolecules, and they bind the target biomolecules with relatively strong affinity. Representative ligands include, by way of illustration, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, aptamers, lipids, retinoids, steroids, glycopeptides, glycoproteins, proteoglycans and the like, and synthetic analogues or derivatives thereof, including peptidomimetics, small molecule organic compounds and the like, and mixtures thereof. The ligands can be suitably micropatterned (i.e. micropatternly disposed) onto solid support surfaces (e.g. gold-coated glass slides) and can be used to capture the biomolecules onto such solid support surfaces. Example of a suitable ligand is the adenosine-specific aptamer containing the 39-mer sequence CGG AUG AGA CGC UUG GCG UGU GCU GUG GAG AGU CAU CCG (SEQ ID NO:1).

"Diffractometry" is the analysis and elucidation of the structure of a substance from the scattering pattern produced when a beam of radiation or particles (such as photons, neutrons, or X rays) strikes it. "Immunoseparation diffractometry" is a technique that combines immunoseparation with diffractometry. For example, included in immunoseparation diffractometry would be "immunomagnetic diffractometry," a technique that combines immunomagnetism (as one type of immunoseparation) with diffractometry, using immunomagnetic capture for immobilizing target biomolecules onto desired surfaces, and diffractometry using in situ assembled optical diffraction gratings which are used for detection of target biomolecules by measuring the diffraction intensities caused by illumination. A variety of light sources can be used to produce illumination in the visible or non-visible part of the spectrum. Examples of suitable light sources include lasers, LEDs, etc.

"Diffraction grating" refers to an optical component with a surface covered by a regular pattern of parallel lines, typically separated by a distance comparable to the wavelength of light. Light rays that pass through such a surface are bent as a result of diffraction, related to the wave properties of light. This diffraction angle depends on the wavelength of the light. For practical applications, most gratings have grooves or rulings on their surface rather than dark lines. Such gratings can be either transparent or reflective. For a given grating, light with a larger wavelength generally has a larger diffraction angle. A single wavelength can simultaneously have multiple discrete diffraction angles, called diffraction orders. Diffraction grating is disclosed, e.g., in U.S. Pat. Nos. 5,029,981, 5,335,113, 5,363,238, and 5,629,804, all of which are incorporated herein by reference.

It has been discovered that the combination of immunoaffinity and diffractometry can be used for the detection of biomolecules, e.g. for the detection of diagnostic serum markers, detection of receptor molecules, etc. In particular, immunomagnetic diffractometry, including in situ assembled diffraction grating, can find utility in biomolecular detection. For example, it is possible to produce self-assembled optical diffraction gratings by immunoimmobilization, and then examine the created patterns (e.g., under an optical microscope) to measure optical diffraction intensity of the biomolecules. The measured optical diffraction intensities enable quantification of the biomolecules. Examples of label-free and inexpensive biosensors based on in situ assembled diffraction gratings are disclosed in Chang et al., 2007, *Appl. Phys. Lett.* 90: 233901-1, and in Acharya et al., 2007, *J. Am. Chem. Soc.* 129: 15824-15829, both of which are herein incorporated by reference.

Methods are provided for the development of self-assembled optical diffraction biosensors devoid of microfabrication or enzymatic amplification for the rapid detection of biomarkers. In particular, the optical diffraction biosensors of the present invention can be used for the detection of S-adenosyl homocysteine (SAH), a potential diagnostic marker for cardiovascular disease (Yi et al., 2000, *J. Biol. Chem.* 275: 29318-29323), with a sensitivity limit of 24.5 pg/ml. SAH is a low molecular mass analyte (384 Da) consisting of the nucleoside adenine joined to the amino acid homocysteine (Hcy) via a 5' thioether linkage. In some embodiments of the present invention, the methods include a sandwich binding approach, wherein the target biomolecule is bound by an antibody to a capture ligand that is specific for the target biomolecule. Examples of such capture ligands include various target biomolecule-specific oligonucleotides or peptides. Using the SAH detection example, SAH is bound by an antibody through the Hcy moiety while an adenine specific RNA aptamer binds to the adenine moiety (FIG. 1). "Aptamers" are oligonucleotides or peptide molecules that bind specific target molecules.

FIG. 1 is a schematic representation of the sandwich complex formation according to the present invention. FIG. 1(a):

structure of S-adenosyl homocysteine (SAH). FIG. 1(b): binding of anti SAH-antibody coupled magnetic bead to the homocysteine end of SAH produces a sandwich complex after binding of the adenosine-specific aptamer to the adenosine end of SAH. This can be achieved, e.g., by spotting substrate that includes ligand-containing gold-coated glass slides with a suspension containing biomolecule-antibody immune complexes. These immune complexes can be optionally attached to solid support, e.g. beads. As described below, adenosine aptamer-SAH-Ab bead grating patterns can be produced through specific binding of an SAH analyte by incubating gold-coated glass slides bearing adenosine aptamer micropatterns with SAH-Ab-beads for 10 minutes.

Figure 2:
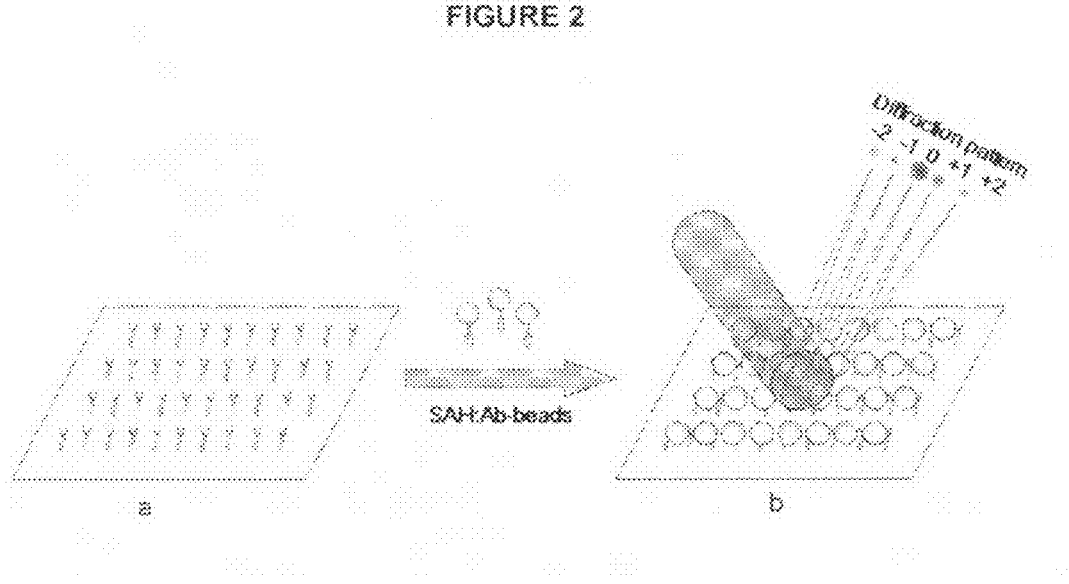
FIG. 2 is a schematic representation of one embodiment of the detection strategy.

In some embodiments, novel methods are provided that use antibody-coupled beads to capture SAH from solution while aptamer-functionalized micropatterns specific for adenine are stamped on a gold-coated glass slide (e.g. gold chip). Based on these specific interactions, SAH bound to the Ab-beads produces a self-assembled optical diffraction grating upon exposure to the aptamer-functionalized micropatterns (FIG. 2). In the schematic presentation of the detection strategy, shown in FIG. 2, the high affinity adenosine-specific aptamer containing the 39-mer sequence CGG AUG AGA CGC UUG GCG UGU GCU GUG GAG AGU CAU CCG (SEQ ID NO:1) is chosen as the capture ligand for the SAH adenine moiety (binding constant: $5 \times 10^{-8}$ M). The aptamer is immobilized, e.g. by coupling biotin to its 5' end, and exposure onto streptavidin-saturated micropatterns. There are various ways of microprinting, i.e. of creating micropatterns, which are known in the art. For example, it is possible to use PDMS stamps to achieve desired micropatterning. "PDMS stamps" are pieces of polydimethylsiloxane (PDMS) that have been patterned usually against a master to form a relief pattern. These stamps are typically used in soft lithography.

A rapid method for the detection of biomolecules (e.g. SAH) using self-assembled optical diffraction gratings has been developed. From an analytical methods perspective, there are several advantages provided by this detection strategy. The analyte becomes concentrated on the surface of the antibody coupled-bead, where it can bind strongly to the micropatterned capture surface via multivalent interactions with the microcontact printed aptamer layer. This produces a rugged optical diffraction grating mediated by antibody ↔ analyte ↔ aptamer self-assembly. Naive aptamer micropatterns do not show a diffraction pattern. Distinct and measurable diffraction patterns are obtained only when biomolecule-antibody (e.g. SAH-Ab) beads are exposed to adenosine aptamer micropatterns.

The biomolecule detection methods described herein are quick, lack the need for special labeling or signal amplification, and possess excellent detection sensitivity. Using the detection of SAH as an example, the fluorescence-based coupled enzyme assay for homocysteine could detect a minimum of 1 µM (Wang et al., 2005, *Biochem. Biophys. Res. Comm.* 331: 351-356), while the SAH detection sensitivity of liquid chromatography/mass spectrometry-based method is 50 nM (Salyan et al., 2006, *Anal. Biochem.* 349: 112-117). Capillary electrophoresis and stable-isotope dilution liquid chromatography-electrospray injection tandem mass spectrometry methods are capable of detecting SAH concentrations as low as 7.2 nM and 1 nM, respectively (Sbrana et al., 2004, *Electrophoresis* 25: 1518-1521; Gellekink et al., 2005, *Clinical Chem.* 51: 1487-1492). In comparison, according to the methods of the present invention, using self-assembled diffraction gratings could detect as low as 64 pM of SAH.

It is known that magnetic beads enable rapid concentration and isolation of the target molecules (Haukanes and Kvam, 1993, *Bio-Technology* 11: 60-63) and hence such beads can be used as target capture and grating-forming agents. A schematic presentation of the immunomagnetic biomolecule binding and the formation of diffraction gratings are illustrated in FIG. 2. The well-defined magnetic bead patterns can function as optical diffraction gratings and can be used for diffraction intensity measurements. Shown in FIG. 2(a) are patterns of aptamer microcontact printed on gold chip. Shown in FIG. 2(b) is how SAH-bound magnetic beads self-assemble onto the aptamer micropatterns to form diffraction gratings that upon illumination (e.g. with a laser) give a characteristic diffraction pattern. Thus, in some embodiments, also provided is an integrated detection system that combines immunomagnetic capture and optical diffraction for rapid detection of biomolecules, e.g. biomarkers, and in particular cancer biomarker. In this detection system, the magnetic beads function not only as regular immunomagnetic capture agents, but also as motifs for the in situ assembly of optical diffraction gratings. The magnetic beads, because of their large size compared to the target molecules, significantly enhance the signal intensity upon diffraction grating formation, thereby greatly lowering analyte detection limits. This magnetic microbead detection system is rapid, simple, inexpensive, devoid of complex microfabrication procedures, and is ultrasensitive. In some embodiments, the magnetic bead integrated optical diffraction methods of the present invention can detect as low as 700 fM (about 20 pg/ml) folate receptor (FR), a cancer biomarker circulating in blood (Eichner et al., 1978, *Am. J. Clin. Nutr.* 31: 1988-1992), without requiring any fluorescent or radio labels, or additional signal amplification steps. The magnetic bead integrated optical diffraction methods of the present invention can be used for the detection of a variety of desired biomarkers, using the methods of the present invention. An additional advantage of these systems and methods is that the primary target capture occurs in solution (not on a surface), allowing mass transport in three dimensions and circumventing reduced reaction rates that result being forced to capture the analyte and associated amplification agents on a surface (two dimensions). Furthermore, these new systems and methods are relatively robust, rapid (both to setup and to operate), inexpensive, and capable of adaptation for point-of-care diagnostics.

The self-assembly of magnetic particles onto suitable micropatterns to form diffraction gratings can be suitably used for the practice of the present invention. Thus, in some embodiments, the self-assembly of analyte-containing microbeads in an alternating line pattern may form a solid diffraction grating which in turn affects the intensity of diffracted light and enables detection of biomolecular targets in femtomolar-level concentrations. Since biological molecules are generally of a few nanometers in size, their sole binding (without any solid particles) to a solid surface results in a relatively weak diffraction patterns. The use of micron-sized magnetic particles (e.g. beads) for molecular separation inherently circumvents this drawback. Hence, the use of magnetic particles play a dual role: (a) as agents of immunomagnetic capture from complex mixtures, and (b) as in situ generated optical diffraction gratings allowing direct, fluorescence or radio label-free detection. Using the detection of FR as an example, as shown below, distinct and measurable diffraction patterns are obtained only when the FR-beads self-assembles on the F-BSA patterns. A comparison with some common detection assays reveals that the method possesses excellent detection sensitivity. Surface plasmon resonance has been shown to detect as low as 130 ng/ml of FR (Indyk and Filonzi, 2004, *J. Agric. Food Chem.* 52: 3253-3258). Enzyme-linked immunosorbent assays (ELISA) can detect as little as 5-100 ng/ml, and improved detection sensitivities have been reported with gold nanoparticles and chemiluminescent substrates (Bao et al., 2006, *Anal. Chem.* 78: 2055-2059). With a quartz crystal microbalance (QCM) biosensor using gold nanoparticles as a signal amplification element, a detection limit of 1.5 ng FR/ml has been achieved, while an enzyme-amplified diffraction-based immunoassay has been reported to detect as low as 50 pg/ml of digoxin (Henne et al., 2006, *Anal. Chem.* 78: 4880-4884; Loo et al., 2005, *Anal. Biochem.* 337: 338-342). Most of the presently available detection methods use time consuming labeling or sequential signal amplification procedures (after capturing target molecules on a solid surface) in order to detect molecules in low quantities. In comparison, the systems and methods using optical diffraction in combination with immunomagnetic capture can detect as low as 700 fM FR (20 pg/ml) without requiring any sequential labeling or amplification procedures.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Example 1

This example illustrates the ultrasensitive detection of S-adenosyl homocysteine (SAH), a potential diagnostic marker for cardiovascular disease. Concentrations of SAH as low as 24.5 pg/ml were detected.

Materials

Gold-coated glass slides obtained from Asylum Research (Santa Barbara, Calif.) were cut into 1.5 cm×1 cm chips. The surfaces of the slides were cleaned with ethanol and dried prior to use. N-Hydroxy succinimide (NHS)-activated magnetic beads (968 nm mean diameter) were obtained from Chemagen (Baesweiler, Germany). SAH and homocysteine (Hcy) were purchased from Sigma Chemical Co. (St. Louis, Mo.). Biotin-BSA and streptavidin were obtained from Pierce Biotechnology (Rockford, Ill.). Adenosine aptamer was synthesized by IDT (Integrated DNA Technologies) (Coralville, Iowa). Optical microscopic studies were performed on a Nikon (Eclipse 80i) microscope. Silicone elastomer kit (SYLGARD 184) was obtained from Dow Corning Corporation (Midland, Mich.).

Diffractometry Setup

Figure 3:
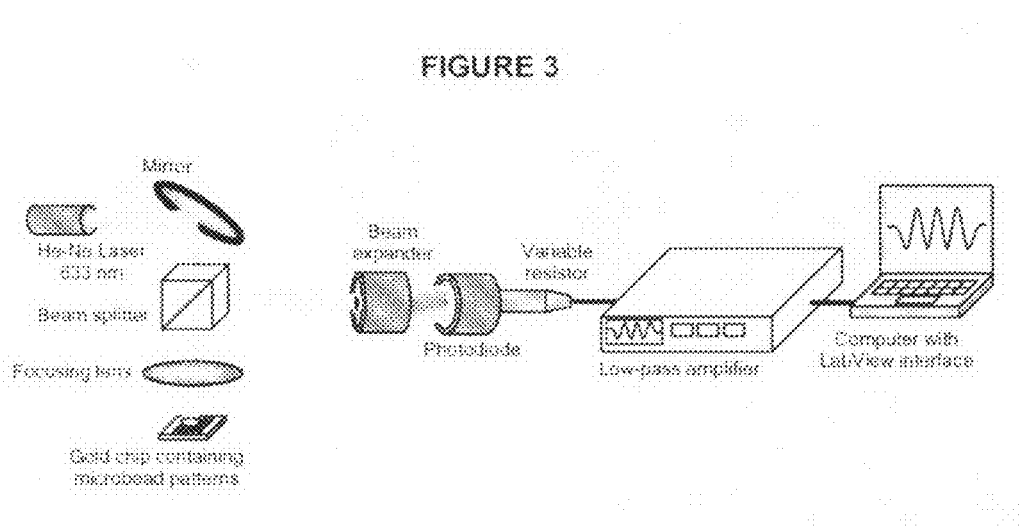
FIG. 3 is a schematic of the optical diffraction measurement system.

FIG. 3 is a schematic of the optical diffraction measurement system. A He—Ne laser (Newport R-30991, 633 nm, 5 mW; Newport, Irvine, Calif.) was focused through a convex lens to obtain a beam diameter of approximately 150 µm on the sample surface. A beam splitter and a set of concave and convex lenses with appropriate focal lengths were used to separate the modes of the diffraction pattern and focus them onto the photodiode. A silicon photodiode with 12 V reverse-bias (Thorlabs DET110; Thorlabs, Newton, N.J.) in conjunction with an adjustable aperture (Thorlabs SM1D12) and a bandpass filter (Thorlabs FL632.8-10) was fixed on a translation stage (Thorlabs MT3) and adjusted to measure the intensities of each mode of the diffraction pattern. The photodiode was connected to a variable resistor (10 KΩ) to convert the output current into a voltage signal. The resulting signal in turn was fed into a low-pass filter/amplifier Stanford Research SR640 (Stanford Research Systems, Sunnyvale, Calif.) and the data processed by a computer operating a National Instruments LabView interface (National Instruments Corporation, Austin, Tex.).

Microcontact Printing of B-BSA

The surface of the polydimethylsiloxane (PDMS) stamp was exposed to a solution of B-BSA (1 mg/ml of PBS) with a cotton swab for 2 min followed by drying the stamp with nitrogen gas. The B-BSA inked stamp was pressed against the gold-coated slide for 2 min to obtain a well-defined pattern. At the end of this period, the stamp was removed and the gold-coated slide was rinsed with PBS and dried.

Saturating the Micropatterns with Streptavidin

The gold chip microcontact printed with B-BSA was dipped into streptavidin solution (1 mg/ml PBS) for 15 min followed by rinsing with PBS and drying under a gentle stream of nitrogen. This step saturated all the biotin groups present on the micropatterns with streptavidin. The gold-coated slides with streptavidin-saturated micropatterns were used for immobilizing biotin-coupled aptamer.

Saturating the Micropatterns with Biotin-Coupled Aptamer

Onto the gold-coated slides containing streptavidin saturated micropatterns, 50 µl of SAH-aptamer solution (1 mg/ml in RNA buffer [300 mM NaCl, 25 mM, Tris, pH 7.6, and 5 mM $MgCl_2$]) was applied with a micropipette, and incubated at room temperature for 15 min. At the end of this period, the slides were rinsed with DNA buffer to remove any unbound SAH-aptamer sticking to the gold surface.

Bead-Based Capture of SAH

From a stock solution, a series of concentrations (40 nM to 64 pM) of SAH solutions were prepared in HEPES buffer (1 M, pH 7.3). An aliquot of Ab beads ($1.8 \times 10^8$ beads suspended in 10 µl of PBS) was transferred into a 1 ml eppendorf tube in a magnetic separator and the liquid was removed. SAH solution (50 µl) in HEPES was added to the neat Ab-beads ($1.8 \times 10^8$) and gently stirred for 30 min, followed by rinsing with HEPES to remove unbound SAH. The beads were resuspended in 50 µl HEPES.

Self-Assembly of SAH-Ab Beads on Aptamer Micropatterns

The SAH-Ab bead suspension ($1.8 \times 10^8$ beads in 50 µl of HEPES) was spotted with a micropipet onto gold-coated slides containing aptamer micropatterns. After 10 min, the slides were rinsed with HEPES and nanopure water, and dried with nitrogen gas. The chips were examined under an optical microscope for micropatterns containing magnetic beads.

SAH molecules dissolved in a buffer solution were isolated by SAH antibody-coupled magnetic beads (Ab beads). Coupling of the SAH-specific antibody to the magnetic beads was performed by treating an antibody solution with NHS-activated magnetic beads. These Ab beads were then used to isolate SAH dissolved in 4-(2-Hydroxyethyl) piperazine-1-ethane sulfonic acid (HEPES) buffer (pH 7.3). SAH solutions of a series of concentrations from 40 nM to 64 pM were prepared in HEPES buffer and each SAH solution of specific concentration was treated with an aliquot of magnetic beads ($1.8 \times 10^8$ beads) for 10 min. At the end of this period, the beads were rinsed with HEPES buffer and used for in situ grating assembly.

Figure 4:
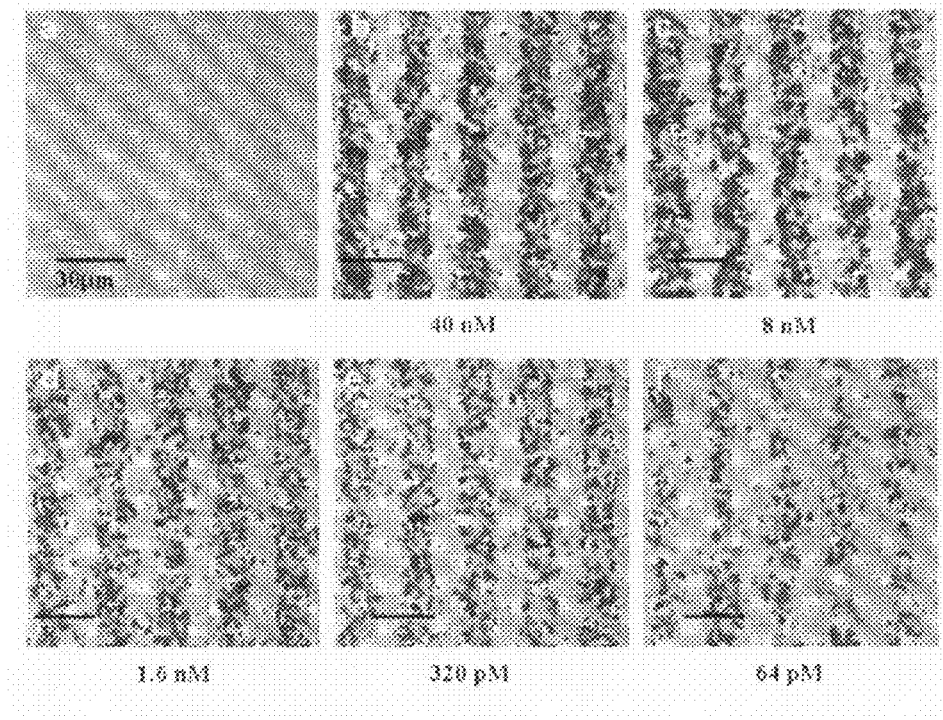
FIG. 4 shows images of self-assembled diffraction gratings.

Adenosine aptamer micropatterns were deposited on gold-coated glass slides using a microcontact printing (µCP) process (Xia and Whitesides, 1998, *Annu. Rev. Mater. Sci.* 28: 153-184; Renault et al., 2002, *Angew. Chem. Int. Ed.* 41: 2320-2323). Onto the gold-coated glass slides (gold chip) bearing the adenosine aptamer micropatterns, a suspension of SAH-Ab-beads was spotted. Incubation of the SAH-Ab-beads for 10 min produced adenosine aptamer-SAH-Ab bead grating patterns due to specific binding of the SAH analyte. The gold chips containing grating patterns were rinsed with HEPES buffer, deionized water, dried, and examined under an optical microscope (FIG. 4). A PDMS stamp with 15 μm wide alternating linear patterns was initially inked with biotin-coupled bovine serum albumin (B-BSA) solution. Micropatterns of B-BSA were then produced on the gold-coated surface by pressing the inked stamp into contact with the slide. Since BSA binds to gold surfaces with high affinity (Henne et al., 2006, *Anal. Chem.* 78: 4880-4884), solid micropatterns with a high density of biotin are produced using this μCP technique. The B-BSA micropatterned slide was then dipped in streptavidin solution to saturate the biotinylated sites. It was subsequently dipped into a biotin-coupled adenosine aptamer solution in RNA buffer for 15 minutes to saturate the biotin binding sites of streptavidin with biotin coupled adenosine aptamer. After rinsing the slide with RNA buffer, these adenosine aptamer micropatterned surfaces were ready for grating assembly by exposure to SAH-Ab beads. Shown in FIG. 4 are images of self-assembled diffraction gratings. FIG. 4(*a*): neat aptamer micropatterns. FIG. 4(*b-f*): diffraction gratings generated by the self-assembly of SAH-Ab beads on aptamer micropatterns. Scale bars, 30 μm.

Diffraction gratings formed by the SAH-Ab beads binding to the adenosine aptamer-modified surface produced a diffraction pattern upon illumination with laser light. The incident laser beam was adjusted to illuminate five grating periods of 15 μm width and 150 μm length.

Figure 5:
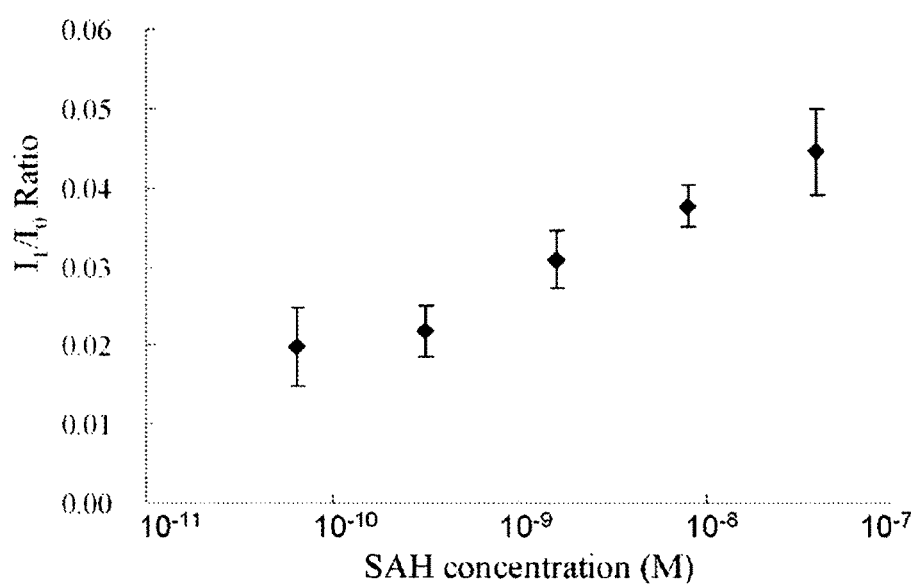
FIG. 5 is a graph showing S-adenosyl homocysteine concentration dependence of normalized diffraction mode ($I_1/I_0$) intensities over the concentration range 64 pM to 40 nM.
Figure 6:
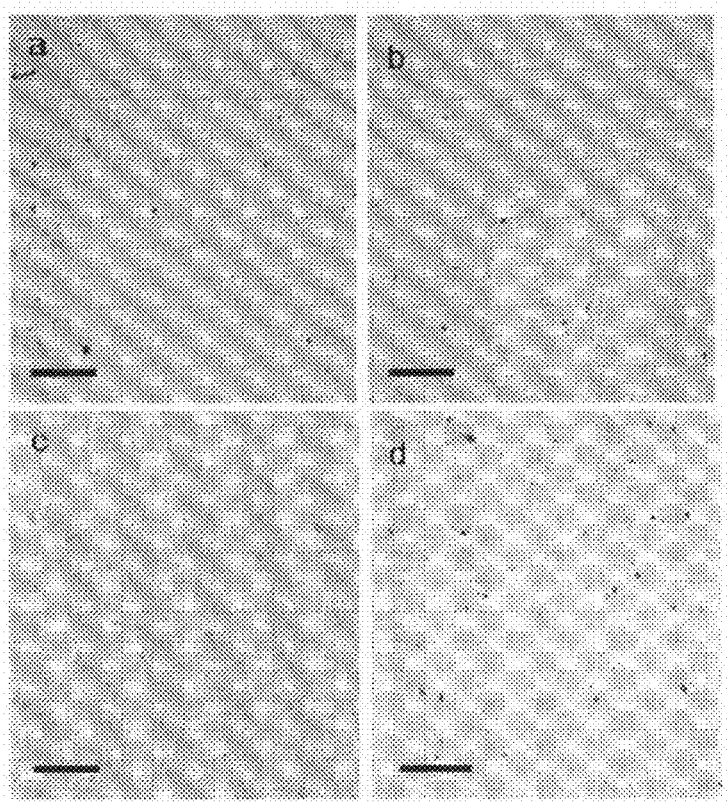
FIG. 6 shows images of SAH detection control experiments.

The SAH concentrations were quantified by comparing the intensities of the diffracted light as a ratio of first mode ($I_1$) to zeroth mode ($I_0$). The number of SAH-Ab beads bound to the aptamer micropatterns on the gold chip decreased with decreasing SAH concentration (FIG. 5). As a consequence, the diffraction mode intensities also decreased. The $I_1/I_0$ values decreased from 0.045 at 40 nM to 0.020 at 64 pM SAH concentrations (FIG. 5). In this configuration, the low concentration limit was 64 pM, beyond which the intensity of the diffraction modes was very weak and their intensities could not be detected by the photodetector.

To validate the mechanism of diffraction grating self-assembly and the specificity of SAH detection, several control experiments were performed. In the absence of SAH, the neat Ab beads did not self-assemble on the aptamer micropatterns, while the SAH-Ab-beads did not bind to the neat streptavidin micropatterns in the absence of adenosine aptamer. In order to examine the requirement of adenine moiety in SAH, homocysteine (Hcy) bound magnetic beads (Hcy-Ab-beads) were used instead of SAH. The homocysteine-bound magnetic beads (Hcy-Ab beads) did not bind in significant amounts on the aptamer micropatterned slides. The absence of magnetic bead self-assembly is attributed to the absence of an adenine moiety in the homocysteine structure to enable adenosine aptamer binding. Similar observations were made when S-adenosylmethionine (SAM) was incubated with Ab-beads before exposure to surfaces micropatterned with adenosine aptamer. This was attributed to the low binding affinity of the anti-SAH antibody for SAM.

Control Experiment 1: Incubation of Ab-Beads onto Aptamer Micropatterns

Onto the aptamer micropatterns generated on gold-coated slides was spotted a suspension of Ab-beads ($1.8 \times 10^8$ beads suspended in 50 μl of HEPES) and incubated for 10 min. At the end of this period, the slides were rinsed three times with HEPES buffer to remove unbound microbeads, once with nanopure water to remove buffer salts, and dried under a gentle stream of nitrogen. The surfaces prepared in this manner were examined under an optical microscope for evidence of magnetic microbead assembled patterns.

Control Experiment 2: Incubation of SAH-Ab Beads on Streptavidin Micropatterns

The SAH-Ab beads ($1.8 \times 10^8$ beads suspended in 50 μl of HEPES buffer, after being exposed to 1 μM SAH) were transferred with a pipet onto gold-coated slides containing streptavidin micropatterns and incubated for 10 min. Again, the chip was rinsed three times with HEPES, once with nanopure water, and dried under a gentle stream of nitrogen.

Control Experiment 3: Exposure of Homocysteine (Hcy)-Bound Beads onto Aptamer Patterns The Ab-beads ($1.8 \times 10^8$) were treated with Hcy solution (50 μl, 1 μM in HEPES, 30 min) followed by rinsing and resuspension in HEPES (50 μl). The Hcy-Ab beads obtained were transferred onto gold-coated slides containing aptamer micropatterns and incubated for 10 min. At the end of this period, the gold chip was rinsed three times with HEPES, once with nanopure water, and dried under a gentle stream of nitrogen gas.

Control Experiment 4: Assembly of S-Adenosylmethionine (SAM)-Bound Beads onto Aptamer Patterns The procedure was exactly the same as control experiment 3, except that the Ab-beads were treated with S-adenosylmethionine (SAM) solution (50 μl, 1 μM in HEPES, 30 min).

Example 2

Several types of cancers over-express specific proteins on the tumor cell surface which enter the blood stream and serve as clinical biomarkers for neoplastic lesions. The folate receptor (FR) is over-expressed in many cancer cell types and increased levels have been found in the serum of cancer patients. This example illustrates the ultrasensitive detection of FR (detected concentrations of FR as low as 20 pg/ml, i.e. 700 fM) using the novel biosensor and the novel magnetic bead-based optical diffraction method, without secondary labeling or multiple signal enhancement steps. The potential of this method in clinical diagnostics was demonstrated by testing blood samples from cancer patients having different stages of cancers.

Materials

Gold-coated glass slides (50 nm thick gold layer with 5 nm thick Chromium as an intermediate layer between glass and gold) were purchased from Asylum Research, and were cut into 1.5 cm×1 cm chips. These gold chips were cleaned with ethanol and dried prior to use. PBS was purchased from GIBCO (Invitrogen, Carlsbad, Calif.). NHS-activated magnetic beads (968 nm mean diameter) were obtained from Chemagen. FR was purchased from Scripps Research Institute. The FR-antibody was obtained from Endocyte Inc. (West Lafayette, Ind.). BSA and folic acid were purchased from Sigma. Fetal calf serum was obtained from Atlanta Biologicals (Lawrenceville, Ga.). Micro BCA protein assay reagent kit was purchased from Pierce Biotechnology. Blood samples from patients with ovarian cancer were obtained under the auspices of an IRB-approved protocol at the Mayo Clinic, Rochester, Minn. Optical micrographs were obtained using Nikon (Eclipse 80i) microscope connected to a CCD camera. Laser scanning confocal fluorescence images were acquired using an MRC-1024 UV (Bio Rad, Hemel Hempstead, England) on a Diaphot 300 (Nikon, Tokyo, Japan) inverted microscope using a 20×0.75 NA lens. The 488 nm wavelength of the krypton-argon laser (Ion Laser Technology) was used to excite the green fluorochrome. Green fluorescence was collected with a 525/35 nm band pass filter.

Diffractometry Setup

The schematic of the instrument setup is presented in FIG. 3. A laser beam (He—Ne laser, Newport R-30991, 633 nm, 5 mW) was passed through a beam splitter (Thorlabs, BS016) and a convex lens (focal length 60 mm) to obtain an incident beam diameter of ~150 μm on the gold chip surface. The reflected beam was passed through a beam expander (Edmund Optics) to separate the modes of the diffraction pattern and focus them onto the photodiode. A silicon photodiode (12 V reverse bias, Thorlabs DET110) affixed with an adjustable aperture (Thorlabs SM1D12) and a bandpass filter (Thorlabs FL632.8-10) was fixed on a translational stage (Thorlabs MT3) for fine adjustments. The photodiode was connected to a variable resistor (10 KΩ, Thorlabs) to convert the output current into voltage, which was in turn fed into a low-pass amplifier (Stanford Research SR640) and the data was processed by a computer with a National Instruments Lab View interface.

Preparation of FR-Antibody Coupled Magnetic Beads (Ab-Beads)

To the FR-antibody solution (1 mg/ml in PBS, 7.2 pH) were added N-Hydroxy succinimide (NHS) activated magnetic beads ($1.8 \times 10^{10}$ beads/ml, mean diameter of 968 nm, obtained from Chemagen) and shaken for 2 h. At the end of this period, the suspension was placed in a magnetic separator and washed with PBS three times and resuspended in PBS. The unreacted NHS groups present on the magnetic beads were quenched by treating with ethanolamine (0.5 mM solution in PBS) followed by rinsing three times with PBS and resuspension in 1 ml of PBS. The Ab-bead suspension was stored at 4° C.

Immunomagnetic Capture of FR

A series of concentrations (10.56 nM to 0.68 pM) of FR dissolved in serum solution (10% fetal calf serum in PBS) were used in the experiments. A suspension of Ab-beads ($1.8 \times 10^8$ beads in 10 μl of PBS) was transferred into a 1 ml eppendorf tube, placed in a magnetic separator, and the liquid was completely removed. To the neat Ab-beads thus obtained was added 50 μl of FR solution in serum and shaken for 15 min. At the end of this period, the eppendorf tube containing the magnetic bead suspension was again placed in a magnetic separator and washed with PBS (3×50 μl) to remove unbound FR and resuspended in 50 μl PBS. The FR-beads thus obtained were used for the in situ assembly of diffraction gratings on F-BSA micropatterns.

Construction of PDMS Stamp

PDMS stamps were prepared with a master mold having 15 μm alternating stripes. The negative mold was designed to give the resulting stamp 15 μm wide stripes. Silicone elastomer base (SYLGARD 184 SILICONE Elastomer Kit, Dow Corning Corporation) and curing agent were mixed in a 10:1 ratio, degassed for 1 h, and then poured into the master. Curing was carried out at 60° C. for overnight. The cured PDMS stamp was carefully peeled off the mold after cooling to room temperature. The stamp was thoroughly rinsed with nanopure water, dried with nitrogen gas, and stored in a vacuum desiccator prior to use.

Microcontact Printing of F-BSA

The F-BSA (1 mg/ml in PBS, pH 7.2) solution was applied onto the PDMS stamp surface with a Q-Tips cotton swab and left to stand for 2 min. F-BSA was prepared according to a published procedure (Henne et al., 2006, *Anal. Chem.* 78: 4880-4884). Excess solution was removed by drying the stamp under a gentle stream of nitrogen gas. The stamp was brought into contact with a gold chip and gently pressed to make a good contact between both surfaces. The stamp was removed after 2 min, and the gold chip was rinsed with PBS to remove any unbound F-BSA.

Self-Assembly of FR-Beads on F-BSA Micropatterns

A suspension of FR-beads ($1.8 \times 10^8$ beads in 50 μl of PBS) was transferred onto a gold chip containing F-BSA micropatterns and incubated for 10 min. At the end of this period, the gold chip was rinsed with PBS, once with nanopure water (to remove buffer salts) and dried under a gentle stream of nitrogen.

Exposure of FR-Beads on Neat BSA Micropatterns

The neat BSA micropatterns were prepared by following exactly the same procedure as that for F-BSA micropattern preparation substituting BSA for F-BSA. The FR-beads were assembled on neat BSA micropatterns following exactly the same procedure as described under "Self-assembly of FR-beads on F-BSA micropatterns."

Exposure of Ab-Beads on F-BSA Micropatterns

Ab-beads were transferred onto the gold chip containing F-BSA micropatterns ($1.8 \times 10^8$ beads suspended in 50 μl of PBS) and incubated for 10 min. At the end of this period, the chip was rinsed with PBS, nanopure water, and dried with nitrogen.

Folate Competition Experiments

An FBP solution (50 μl, 50 nM) in 10% fetal bovine serum was added to Ab-beads (same quantity and preparation as described before) and shaken for 15 min. At the end of this period, the FBP-beads were rinsed with PBS (3×50 μl) in a magnetic separator and the liquid was completely removed. To the neat FBP-beads was added folate-FITC solution in PBS (50 μl, 200 nM) and shaken for 15 min. At the end of this period the magnetic beads were rinsed with PBS (3×50 μl) in a magnetic separator and resuspended in 50 μl of PBS. Another sample was prepared by following exactly the same procedure but using 25 nM of folate-FITC. The folate-FITC treated FBP-beads were separately transferred on to two gold chips containing F-BSA micropatterns and incubated for 10 min followed by rinsing with PBS, nanopure water, and dried with nitrogen gas.

Experiments with Blood Samples of Cancer Patients

The serum was separated from the blood sample by centrifugation and diluted 10-fold for direct comparison with experiments which were performed by adding target molecules to 10% sera. The experiments involving immunomagnetic separation of FR and the assembly of FR-beads onto F-BSA patterns were performed by following exactly the same procedures as described earlier.

Immunomagnetic Capture of FR from Serum

The FR-antibody coupled magnetic beads (Ab-beads) were used for the immunomagnetic separation of FR from serum. Ab-beads were prepared by reacting NHS-activated magnetic beads with FR-antibody solution. The unreacted NHS groups present on the magnetic beads were then quenched by addition of ethanolamine.

FR present in 10% fetal calf serum in PBS was immunomagnetically captured on Ab-beads. Aliquots of Ab-beads were separately incubated with increasing concentrations of FR solutions (11 nM to 700 fM) for 10 min while maintaining a constant number of Ab-beads ($1.8 \times 10^8$ beads), followed by rinsing with PBS in a magnetic separator to remove unbound FR and obtain pure FR-bound beads (FR-beads).

In Situ Assembly of Optical Diffraction Gratings

FR specifically binds to folic acid in 1:1 ratio with strong affinity ($K_d = 10^{-10}$ M). Accordingly, patterns of folate coupled bovine serum albumin (F-BSA) were microcontact printed onto gold-coated glass slides (gold chip) as a FR-recognition element. F-BSA binds strongly to gold surfaces, providing a robust micropattern upon printing with an elastomeric stamp containing 15 μm wide alternating linear patterns (Henne et al., 2006, *Anal. Chem.* 78: 4880-4884;

Renault et al., 2002, *Angew. Chem. Int. Ed.* 41: 2320-2323). Importantly, F-BSA was deposited only in the direct contact areas on the gold chip, rendering the micropatterns as well-defined templates for self-assembly of FR-beads.

Figure 8:
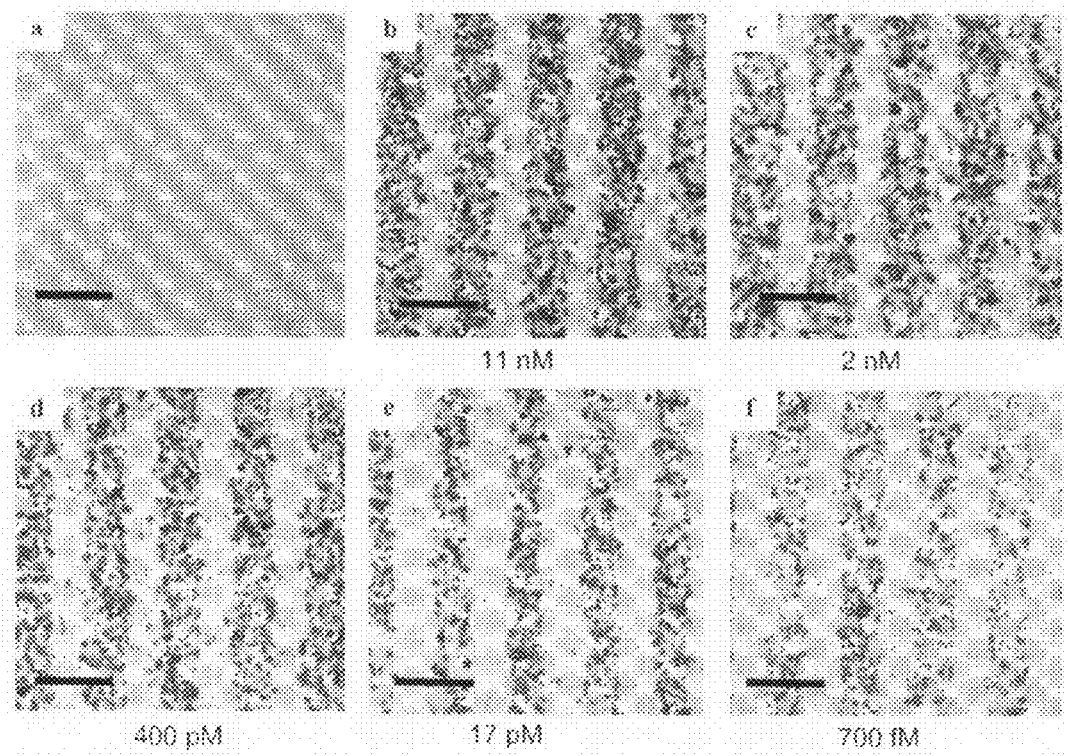
FIG. 8 shows optical micrographs of in situ assembled diffraction gratings.

A suspension of FR-beads in PBS was transferred onto a gold chip containing F-BSA micropatterns for the in situ assembly of an optical diffraction grating. FR-beads were observed to specifically attach to the F-BSA micropatterns, while unbound FR-beads could be readily removed by rinsing with PBS. Finally, the gold chip was rinsed with nanopure water to remove buffer salts and dried under a gentle stream of nitrogen. The FR-bead micropatterns were characterized by optical microscopy (FIG. 8). These well-defined and robust magnetic bead patterns functioned as optical diffraction gratings and were used for diffraction intensity measurements. FIG. 8 shows optical micrographs of in situ assembled diffraction gratings. FIG. 8(a): micropattern of folate-BSA stamped onto a gold chip. FIG. 8(b-f): diffraction gratings formed by FR-beads following their self-assembly on folate-BSA printed patterns. Packing density of FR-beads decreases with decreasing concentrations of FR from 11 nM to 0.7 pM. Scale bars, 30 μm.

Optical Diffraction Measurements

The optical diffraction-based FR detection method is illustrated in FIG. 7 and includes: immunomagnetic capture of FR from serum; in situ assembly of optical diffraction gratings; and optical diffraction intensity measurements. The FR present in the serum solution was immunomagnetically captured by magnetic beads. FIG. 7(a): microcontact printed folate-BSA patterns. FIG. 7(b): self-assembled FR-beads form diffraction gratings on folate-BSA micropatterns. Illumination with a laser then yields a characteristic diffraction pattern whose modal intensities correspond to the density of attached beads.

Self-assembly of FR-beads onto F-BSA micropatterns generated an optical diffraction grating surface that consisted of a row of diffraction modes of varying intensities (FIG. 7) due to the interference of laser light beams that reflected from the beads and bare gold surface. Monitoring the intensities of the diffraction modes enabled the quantitative measurement of binding. The schematic of the diffractometry set up is presented in FIG. 3. The intensity of the diffraction modes varied with the packing density of the micropatterns. The number of magnetic beads self-assembled onto the micropatterns decreased with decreasing concentration of FR, leading to loosely formed micropatterns and decreasing diffraction intensities (FIG. 8).

The intensity ratio of the first and the zeroth modes i.e., $I_1/I_0$, versus the concentration of FR, was examined. The binding of beads increased the first diffraction mode signal with respect to the zeroth mode, resulting in an increase in the diffraction efficiency. Normalizing the modal intensities in this way also served to suppress the effects of possible drifts in incident laser intensity and small variations from sample to sample. To examine the potential of this biosensor in clinical diagnostics, two blood samples (A & B) from two cancer patients diagnosed with different stages of cancer were tested. For appropriate comparison with the serum experiments described above, the patients' sera were diluted tenfold in PBS.

Figure 9:
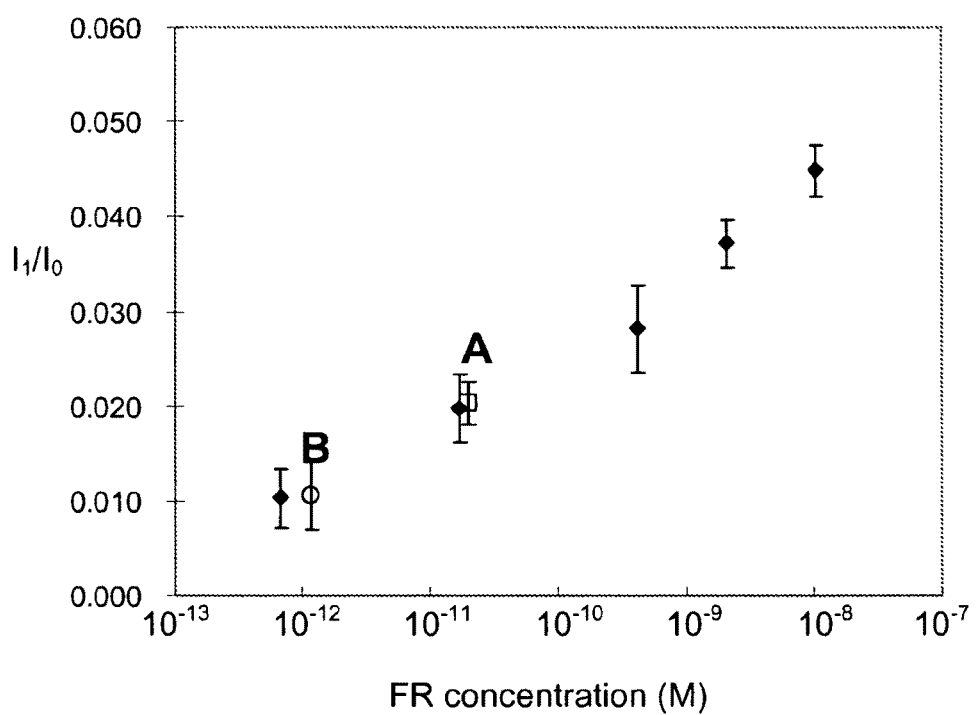
FIG. 9 is a graph showing the variation of normalized diffraction intensity ($I_1/I_0$) with folate receptor (FR) concentration.

FIG. 9 illustrates variation of normalized diffraction intensity ($I_1/I_0$) with FR concentration. The diffraction intensity increases with FR concentration from 0.7 pM to 11 nM. In FIG. 9, sample A (□) corresponds to an approximate FR concentration of 20 pM, while that of sample B (○) is ~1 pM.

As can be seen from the plot (FIG. 9), the $I_1/I_0$ value decreased from 0.045 to 0.01 over the 11 nM to 700 fM concentration range.

Figure 10:
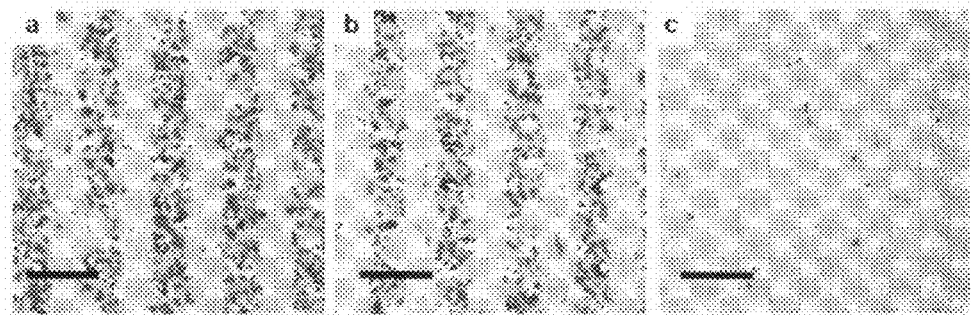
FIG. 10 shows images of analysis of diluted blood samples obtained from cancer patients (a, b) and a control sample obtained from a healthy person (c).

FR was immunomagnetically captured from the blood samples using the Ab-beads and rinsed with PBS buffer. The FR-beads were spotted on a gold chip containing the usual F-BSA micropattern. Once again, the FR-beads self-assembled on F-BSA micropatterns forming diffraction gratings, as shown in FIG. 10b, c. Illustrated in FIG. 10 are data from the analysis of diluted blood samples obtained from cancer patients. FIG. 10(a, b): in situ assembled diffraction gratings using immunomagnetically separated FR-beads following their incubation in the serum of two unrelated cancer patients (samples A and B, respectively). FIG. 10(c): diffraction grating was not formed with immunomagnetically separated FR-beads incubated in blood serum of a healthy person (control experiment). Scale bars, 30 μm. The normalized diffraction intensity ($I_1/I_0$) for sample A was 0.02 and for sample B was 0.011. The corresponding concentrations were approximated (by fitting a curve to the previously described serum data) to be about 20 pM and 1 pM, respectively (FIG. 9). The FR concentration in the non-diluted blood sample A determined independently by ELISA was 300 pM (i.e. similar to the 20 pM concentration determined in the 1:10 diluted sample measured by interferometry). Because of the very low levels of FR in sample B, the FR concentration could not be determined with ELISA. As a control, the blood sample obtained from a healthy individual following the same experimental procedure was tested. In this case, FR-beads did not self-assemble on the F-BSA micropatterns in significant amounts, and no diffraction grating formation was observed (FIG. 10d). These results demonstrate the potential of the method as a ultrasensitive and rapid biosensor for clinical diagnostics.

In all experiments, the detection area of the micropattern scanned was 0.0225 mm², comprising five bead-containing stripes, each of 15 μm width and 150 μm length. A characteristic diffraction pattern was obtained only when the FR-beads self-assembled onto the F-BSA patterns. The approximate number of magnetic beads present per detection area varied between 5900 for 11 nM to 3100 for 700 fM concentration of FR. The number of FR molecules captured by a single Ab-bead (for 11 nM FR concentration) was determined from Micro-BCA assay experiments (Smith et al., 1985, *Anal. Biochem.* 150: 76-85) to be ~150. Micro-BCA assay was not sensitive enough to reveal the number of FR molecules captured for FR solutions below 10 nM concentrations. For these concentrations, the number of FR molecules captured by each Ab-bead was roughly estimated by dividing the number of FR molecules theoretically present in an FR solution of a given concentration by the magnetic bead number. The number of FR molecules captured per bead decreased from 150 molecules (at 11 nM) to ~1 molecule (at 0.7 pM). With this method it was possible to detect as few as 3100 molecules per detection area of 0.0225 mm².

Evidence for the Specific Assembly of FR-Beads on F-BSA Micropatterns

In order to demonstrate the requirement of folate ligands for specific binding of FR-beads, BSA (lacking conjugated folate) was microcontact-printed on a gold chip. Onto this chip an aliquot of FR-beads was transferred.

Figure 11:
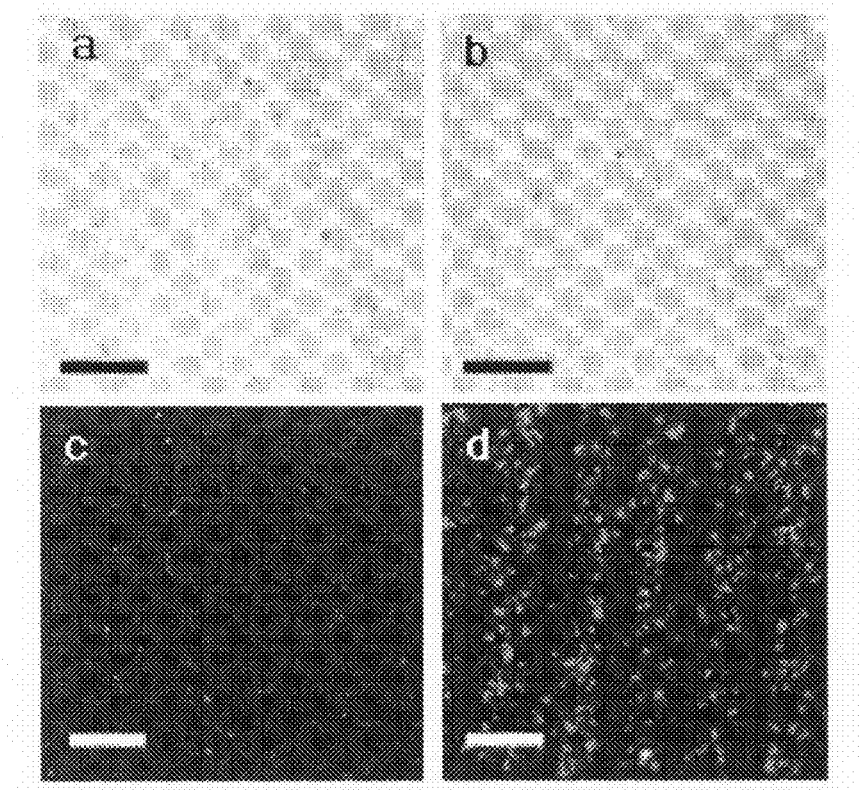
FIG. 11 shows images of control experiments demonstrating the requirement for folate receptor for in situ formation of diffraction gratings.

FIG. 11(a, b) shows control experiments demonstrating the requirement for folate receptor (FR) for in situ formation of diffraction gratings. FIG. 11(a): FR-beads do not bind to underivatized BSA micropatterns in significant numbers, demonstrating the importance of the folate ligand for in situ assembly of a diffraction grating. FIG. 11(b): antibody coupled beads do not bind significantly to the F-BSA micropatterns in the absence of FR.

FIG. 11 (c, d) shows folate competition experiments demonstrating the specific binding of FR to folate. FIG. 11(c): FR-beads saturated with folate-FITC did not self-assemble significantly on F-BSA patterns to form diffraction gratings (FR=50 nM; Folate FITC=200 nM). FIG. 11(d): FR-beads partially saturated with folate-FITC did self-assemble on F-BSA patterns (FR=50 nM; Folate FITC=25 nM). Scale bars, 30 µm.

Optical microscopic examination of the chip revealed that the FR-beads did not bind significantly to the underivatized BSA, thus demonstrating the requirement of folate ligands for in situ assembly of diffraction gratings (FIG. 11a).

To test the specific requirement for capture of FR, a gold chip containing F-BSA micropatterns was incubated with Ab-beads devoid of FR. As expected, Ab-beads did not bind significantly to the F-BSA micropatterns in the absence of FR, demonstrating the requirement of FR (FIG. 11b).

To further confirm the specific binding of FR-beads to folate ligands, competition experiments using fluorescently labeled folate (folate-FITC) were conducted. A suspension of Ab-beads was treated with an FR solution (50 nM in 10% fetal calf serum). The FR-beads were then treated with folate-FITC solution in PBS (200 nM) to saturate folate binding sites. The folate-FITC saturated FR-beads were then transferred onto F-BSA micropatterns. The beads did not bind in significant numbers to the F-BSA micropatterns, confirming the requirement of FR with free folate binding sites (FIG. 11c). A similar experiment was performed with 25 nM folate-FITC to obtain partially saturated FR-beads. These partially saturated FR-beads did self-assemble on F-BSA micropatterns to form loosely packed gratings as they had some folate binding sites available on them (FIG. 11d).

Micro-BCA (Bicinchoninic Acid) Protein Assay

Micro-BCA assay experiments were performed to calculate the number of FR molecules captured by single Ab-bead (for the solution with 11 nM FR). Concentration of FR before and after incubation with Ab-beads was determined using a Micro-BCA protein assay reagent kit (Pierce Biotechnology). A set of protein standards from bovine serum albumin (BSA) were freshly prepared with concentrations ranging from 0 to 200 µg/ml using phosphate buffered saline (PBS) as diluent. The Working Reagent (WR) was prepared according to the instructions provided with the Micro-BCA Kit. One ml of each standard and the FR solutions were pipetted into test tubes, and 1 ml of WR was added to each tube and mixed well. The tubes were covered and incubated at 60° C. for 1 h followed by cooling to room temperature. The absorbance of all the BSA standards and FR solutions was measured within 10 minutes at 562 nm using a spectrophotometer (DU 640 Spectrophotometer, Beckman Coulter, Inc., CA). Neat PBS was used as a blank run.

A standard curve was prepared by plotting the average of the 562 nm readings for each BSA standard vs. its concentration in µg/ml. This standard curve was used to determine the concentration of each unknown FR solution.

Figure 12:
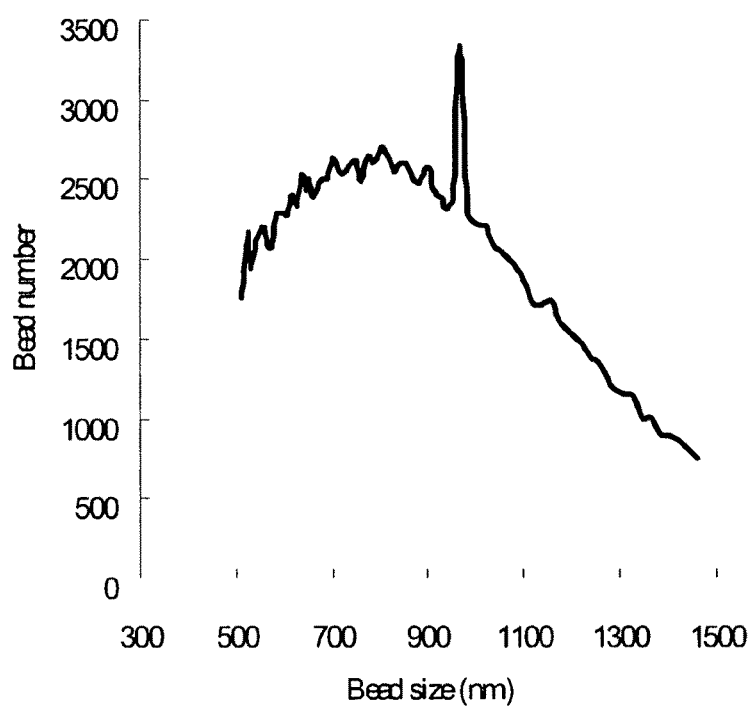
FIG. 12 is a plot depicting the size distribution of N-Hydroxy succinimide (NHS)-activated magnetic beads used in one embodiment of the present invention.

The magnetic bead size distribution of the NHS-activated magnetic beads is shown in the graph in the plot in FIG. 12, which was obtained from Chemagen.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered in bioengineering, molecular biology, biochemistry, and medicine, and obvious to those skilled in the art, are within the scope of this invention. All publications, patents, and patent applications cited herein are incorporated by reference in their entirety for all purposes.

What is claimed is:

1. A system for detecting biomolecules in a sample, the system comprising:
   a) a substrate having a surface with rows of one dimensional diffraction grating patterns, each row separated from another row by the surface of the substrate, each row comprising a plurality of biomolecules coupled to beads
   b) an incident light source for delivering a beam to the substrate surface, thereby illuminating a plurality of the one-dimensional grating pattern rows, causing associated reflections from the illuminated beads and the substrate surface resulting in interference patterns generating a plurality of modes each represented by a dot in a one-dimensional pattern;
   c) an optical detector including a photodiode fixed on a translation stage for detecting light intensity of a first dot representing a first mode ($I_1$) and for detecting a different second dot representing the zero$^{th}$ mode ($I_0$) and a beam expander arranged to receive reflected light from the illuminated beads and substrate surface and to separate the modes of the diffraction pattern and focus the modes on the photodiode; and
   d) a processor configured to compare the ratio ($I_1/I_0$) of the light intensity from the first mode and the light intensity from the second zero$^{th}$ mode to a predefined calibration curve, and determine the concentration of the biomolecules.

2. The system of claim 1, wherein the biomolecule is S-adenosyl homocysteine (SAH), and the system is capable of determining concentration of SAH of as low as about 60 pM.

3. The system of claim 1, wherein the biomolecules coupled to beads are sandwich complexes, each complex comprising:
   i) a biomolecule-specific second molecule microprinted on the substrate surface,
   ii) the biomolecule bound to the biomolecule-specific second molecule at a second-molecule-biomolecule binding site, and
   iii) a biomolecule-specific first molecule bound to the biomolecule at a first-molecule-biomolecule binding site, wherein the biomolecule-specific first molecule is coupled to the bead, and wherein the beads are magnetic.

4. The system of claim 3, wherein the biomolecule-specific first molecules are biomolecule-specific antibodies and the biomolecule-specific second molecules are biomolecule-specific ligands patternly disposed on the substrate surface.

5. The system of claim 3, wherein the biomolecule-specific first molecules bind the biomolecules to produce immune complexes.

6. The system of claim 5, wherein the substrate surface is suitable for self-assembly of one or more immune complexes in a selected pattern.

7. The system of claim 3, wherein the biomolecule-specific first molecules are antibodies or ligands.

8. The system of claim 3, wherein the biomolecule-specific second molecules are antibodies or ligands.

9. The system of claim 1, wherein the substrate surface is a gold-coated glass slide.

10. The system of claim 1, wherein the light source is laser.

11. The system of claim 1, wherein the incident light illuminates at least 5 rows of one dimensional diffraction grating patterns.

12. The system of claim 1, wherein the incident light illuminates at least 2 rows of one dimensional diffraction grating patterns.

13. The system of claim 1, wherein each row of one dimensional diffraction grating pattern is about 15 μm wide and the pitch between two adjacent rows is about 30 μm.

14. The system of claim 1, wherein the first mode is mode ±1 positioned about the zero$^{th}$ mode.

15. The system of claim 2, the calibration curve represents a non-linear relationship between intensity ratio of mode ±1 to the zero$^{th}$ mode ($I_1/I_0$) and SAH concentration ranging from about 0.015 for $I_1/I_0$ representing SAH concentration of about 0.08 nM to about 0.05 for $I_1/I_0$ representing SAH concentration of about 60 nM.

16. The system of claim 1, wherein the optical detector is a charged coupled device.

17. The system of claim 2, the biomolecule-specific second molecule comprises an adenosine-specific aptamer containing comprising SEQ ID NO: 1.

* * * * *

SEQUENCE LISTING

```
<160> NUMBER OF SEQ ID NOS: 1

<210> SEQ ID NO 1
<211> LENGTH: 39
<212> TYPE: RNA
<213> ORGANISM: Artificial Sequence
<220> FEATURE:
<223> OTHER INFORMATION: 39-mer sequence from a high affinity adenosine-
      specific aptamer

<400> SEQUENCE: 1
cggaugagac gcuuggcgug ugcuguggag agucauccg                           39
```